US010741048B1

(12) United States Patent
Foster et al.

(10) Patent No.: US 10,741,048 B1
(45) Date of Patent: Aug. 11, 2020

(54) BEHAVIOR MODIFICATION BRACELET SYSTEM FOR WANDERING PREVENTION

(71) Applicants: Jennifer B. Foster, Fishers, IN (US); Paul C. Mayes, Fishers, IN (US)

(72) Inventors: Jennifer B. Foster, Fishers, IN (US); Paul C. Mayes, Fishers, IN (US)

( * ) Notice: Subject to any disclaimer, the term of this patent is extended or adjusted under 35 U.S.C. 154(b) by 0 days.

(21) Appl. No.: 16/170,116

(22) Filed: Oct. 25, 2018

Related U.S. Application Data

(63) Continuation-in-part of application No. 16/128,576, filed on Sep. 12, 2018.

(60) Provisional application No. 62/557,454, filed on Sep. 12, 2017.

(51) Int. Cl.
*G08B 21/08* (2006.01)
*G08B 21/02* (2006.01)
*G08B 3/10* (2006.01)
*G08B 6/00* (2006.01)

(52) U.S. Cl.
CPC ............ *G08B 21/088* (2013.01); *G08B 3/10* (2013.01); *G08B 6/00* (2013.01); *G08B 21/0261* (2013.01); *G08B 21/0269* (2013.01)

(58) Field of Classification Search
CPC ............................ G08B 21/088; H04B 1/3833
See application file for complete search history.

(56) References Cited

U.S. PATENT DOCUMENTS

| 10,159,849 B2 * | 12/2018 | Kaib ................... G08B 3/10 |
| 2004/0046667 A1 * | 3/2004 | Copley ............ G08B 21/0283 340/573.4 |
| 2010/0309002 A1 * | 12/2010 | Duvall ............. G08B 21/0247 340/573.4 |
| 2015/0164351 A1 * | 6/2015 | He ..................... A61B 5/1102 702/19 |
| 2018/0075716 A1 * | 3/2018 | Mirov ..................... G08B 6/00 |

* cited by examiner

*Primary Examiner* — Qutbuddin Ghulamali
(74) *Attorney, Agent, or Firm* — Matthew M. Googe; Robinson IP Law, PLLC

(57) ABSTRACT

A behavior modification system for deterring an individual from approaching a body includes: a bracelet worn by the individual and including a bracelet controller, an antenna in communication with the bracelet controller, an alert component in communication with the bracelet controller; a base unit including an antenna, a base speaker, and a controller in communication with the base speaker and antenna, the base unit configured to broadcast a predetermined caution zone around a proximity of the base unit. When the controller of the bracelet determines that the bracelet is located within the proximity of the base unit based on a signal received from the base unit on the bracelet, the alert component generates an alert to the wearer of the bracelet, the alert including one or more of arrhythmic vibrations and audible sounds that are unpleasant to an individual with ASD.

11 Claims, 4 Drawing Sheets

BEHAVIOR MODIFICATION BRACELET SYSTEM FOR WANDERING PREVENTION

CROSS-REFERENCE TO RELATED APPLICATION

This application claims priority to and is a non-provisional of U.S. provisional patent application Ser. No. 62/557,454 for a Behavior Modification Bracelet System for Wandering Prevention filed on Sep. 12, 2017 and claims priority to U.S. application Ser. No. 16/128,576 filed on Sep. 12, 2018, the contents of which are incorporated herein by reference in its entirety.

FIELD

This disclosure relates to the field of alert systems. More particularly, this disclosure relates to systems for providing an alert when an individual wanders into an unsafe proximity to a body of water such as a swimming pool.

BACKGROUND

Safety for children is of the utmost importance. However, a child diagnosed with autism spectrum disorder (ASD) present special challenges that have the ability to exacerbate a parent's worst fears. Two of the most challenging behavioral characteristics associated with ASD are wandering and an affinity to enter a body of water. As of April of 2018, the Center for Disease Control and Prevent released new data on the prevalence of autism in the United States. This surveillance study identified 1 in 59 children as having ASD, and a growing trend of drowning deaths is expected as a result.

Currently no technology exists that works in real-time to address wandering related deaths via drowning for those individuals with ASD. Further, other efforts to aid parents of children with ASD are often limited to the following: educational books; movies; school in-services; support groups aimed at awareness; location devices that utilize GPS; and bracelets that provide and promote ASD identification awareness.

The above and other needs are met by a behavior modification bracelet system for preventing wandering and reducing instances of drowning by deterring children, particular those with ASD, from approaching a body of water such as a pool.

SUMMARY

The above and other needs are met by a behavior modification bracelet system for deterring an individual from entering a caution area such as a swimming pool. In a first aspect, a behavior modification system for deterring an individual from approaching a body of water includes: a bracelet worn by the individual and including a bracelet controller, an antenna in communication with the bracelet controller, an alert component in communication with the bracelet controller for providing an alert to the wearer of the bracelet, and a power supply in communication with the bracelet controller; and a base unit including an antenna, a base speaker, and a controller in communication with the base speaker and antenna, the base unit configured to broadcast a predetermined caution zone around a proximity of the base unit. When the controller of the bracelet determines that the bracelet is located within the proximity of the base unit based on a signal received from the base unit on the bracelet, the alert component generates an alert to the wearer of the bracelet, the alert including one or more of arrhythmic vibrations and audible sounds that are unpleasant to an individual with ASD. The base unit emitting an audible alert via the base speaker when the bracelet is located within proximity of the base unit.

In one embodiment, the alert component of the bracelet includes a speaker in communication with the controller. In another embodiment, the alert component of the bracelet includes a vibration motor in communication with the controller. In yet another embodiment, the alert component of the bracelet further includes a vibration motor in communication with the controller.

In one embodiment, the bracelet further includes a GPS module in communication with the controller, wherein the bracelet transmits a geographic location of the bracelet via the GPS module.

In another embodiment, the behavior modification system further includes a user device having a display, one or more inputs, and a processor, the user device in communication with the bracelet and base unit via a network. In yet another embodiment, an alert is displayed on the user device when the bracelet is determined to be in proximity to the base unit. In one embodiment, the caution zone may be determined based on input from the user device.

In another embodiment, the bracelet and base unit communicate via Bluetooth. In yet another embodiment, the base unit is a buoy configured to float within a body of water defined as a caution zone.

In a second aspect, a method of deterring entry of an individual within a caution zone includes: providing a bracelet including an antenna, an alert component, and a controller in communication with the antenna and alert component; providing a base unit including an antenna, a base speaker, and a controller in communication with the base speaker and antenna, the base unit configured to broadcast a predetermined caution zone around a proximity of the base unit; defining a caution zone around the base unit, the caution zone corresponding to a body of water; generating an alert on the alert component of the bracelet when the bracelet is determined to be in proximity to the caution zone around the base unit; and generating an audible alert on the base unit when the bracelet is determined to be in proximity to the caution zone around the base unit.

In one embodiment, the alert generated on the bracelet is an arrhythmic alert generated by a vibration motor of the bracelet.

BRIEF DESCRIPTION OF THE DRAWINGS

Further features, aspects, and advantages of the present disclosure will become better understood by reference to the following detailed description, appended claims, and accompanying figures, wherein elements are not to scale so as to more clearly show the details, wherein like reference numbers indicate like elements throughout the several views, and wherein:

DETAILED DESCRIPTION

Various terms used herein are intended to have particular meanings. Some of these terms are defined below for the purpose of clarity. The definitions given below are meant to cover all forms of the words being defined (e.g., singular, plural, present tense, past tense). If the definition of any term below diverges from the commonly understood and/or dictionary definition of such term, the definitions below control.

Embodiments of the present disclosure include a behavior modification bracelet system for preventing wandering and reducing instances of drowning by deterring children, particular those with ASD, from approaching a body of water such as a pool. The behavior modification bracelet system of the present disclosure utilizes concepts related to the science of Behaviorism to stop and/or minimize a child from entering a body of water.

The behavior modification bracelet system creates a defined caution zone that exists around a body of water. A bracelet worn by an individual who approaches the caution zone receives aversive or unpleasant stimulation from the bracelet worn by the individual. A buoy or other device is placed in the body of water to define the caution zone and create stimulation on the bracelet. A wearer of the bracelet is taught to avoid the caution zone by deactivating unpleasant stimulation from the bracelet when the wearer moves away from the caution zone. Further, when a wearer of the bracelet enters the predetermined caution zone, the following may occur: (1) both arrhythmic vibrations along with a high frequency or high pitch audible sound are emitted from the bracelet; (2) when the bracelet is detected in proximity to the predetermined caution zone, an audible alarm is emitted from the buoy to allow people within the vicinity of the buoy to be alerted to the wearer entering the predetermined caution zone; and (3) an advisory message may be transmitted to a third party device, such as a smartphone, to warn of incursion into the predetermined caution zone and to allow location of the wearer of the bracelet such as with GPS.

Components of the behavior modification bracelet system including an adjustable and waterproof bracelet. In one embodiment the bracelet may be difficult to remove by the wearer to prevent inadvertent removal by the wearer. The bracelet may further include indicator lights, such as LED lights, within the bracelet to indicate a state of the bracelet. Vibratory and auditory stimuli of the bracelet may be adjustable via a smartphone or other user device. Communication between a transmitter located within the bracelet, a receiver in the buoy, and a smartphone or other user device may be via Bluetooth, WiFi, radio transmission, or other similar communication protocols. The bracelet may further include a GPS transmitter for tracking of a location of a wearer of the bracelet.

Figure 1:
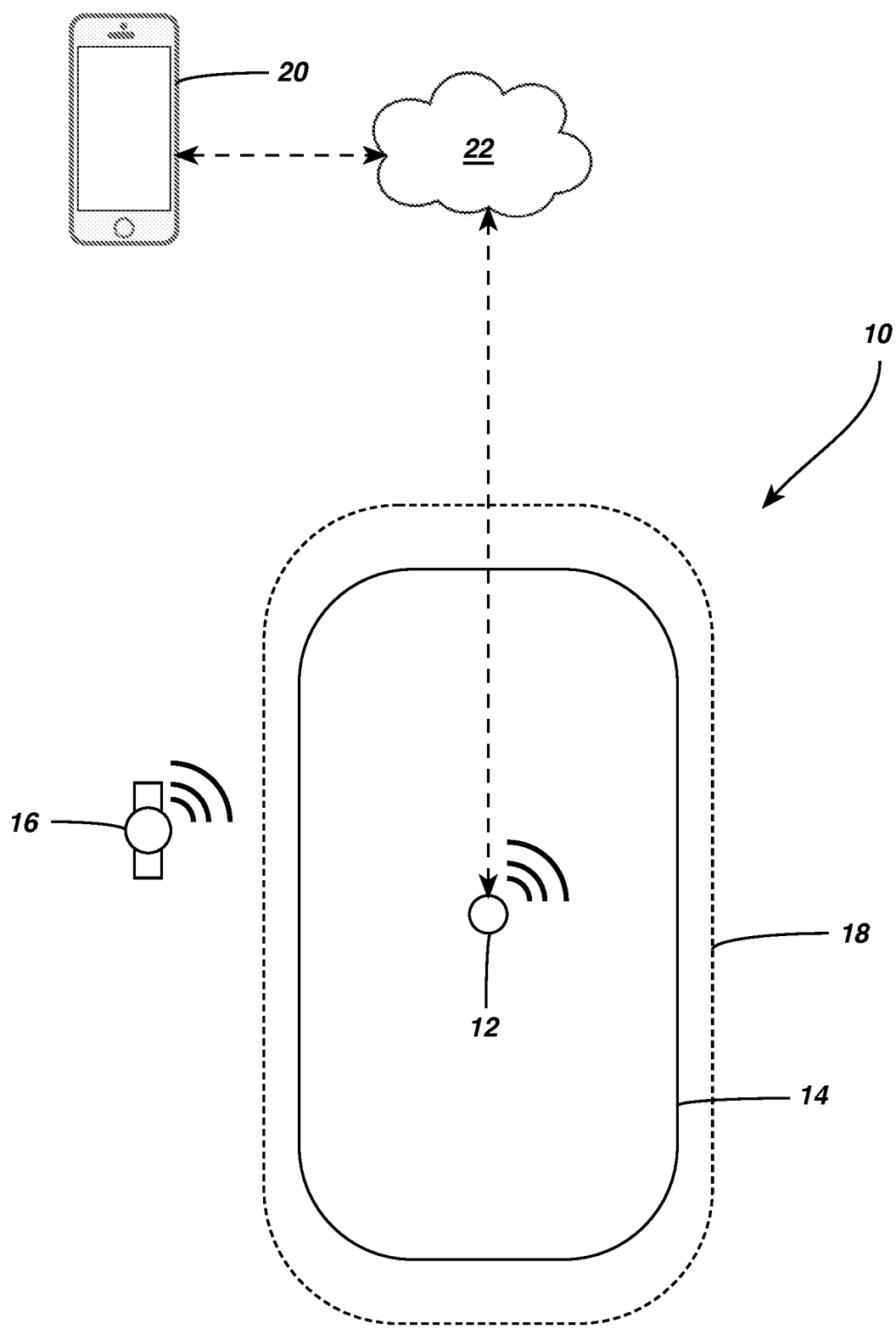
FIG. 1 shows a diagram of a behavior modification bracelet system according to one embodiment of the present disclosure.

Referring now to FIG. 1, a behavior modification bracelet system 10 includes a base unit, which is preferably a buoy 12 that is located within an area of interest, such as a swimming pool 14 or other body of water. A bracelet 16 is also provided and is configured to be worn by an individual, preferably an individual with ASD. A caution zone 18 is defined around the buoy 12 and is preferably sized such that the caution zone 18 is defined around the swimming pool 14. As described above, when the bracelet 16 is in proximity to the buoy 12, such as by entering the caution zone 18 around the swimming pool 14, an alert is generated on the bracelet 16 to deter the individual wearing the bracelet from approaching the swimming pool 14. Further, the buoy 12 may generate an audible alert, and may further communicate with a user device 20 to warn of an incursion into the caution zone 18 by the individual wearing the bracelet 16. The buoy 12 may transmit an alert and otherwise communicate with the user device 20 via a network 22, such as the Internet.

Figure 2:
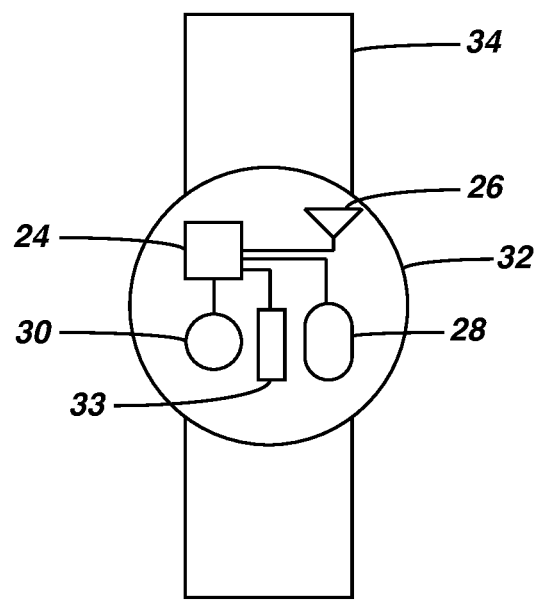
FIG. 2 shows a diagram of a bracelet of a behavior modification bracelet system according to one embodiment of the present disclosure.

Referring to FIG. 2, the bracelet 16 includes a controller 24 that is in communication with various components of the bracelet 16 to determine whether the bracelet 16 is in proximity to the buoy 12 and generate an alert. The bracelet 16 includes one or more antennas 26 in communication with the controller for communicating with the buoy 12. The antennas 26 are preferably configured to communicate with the buoy 12 and determine whether the bracelet 16 is in proximity to the buoy 12. The one or more antennas 26 may further include a GPS antenna for determining a geographic location of the bracelet 16 and the individual wearing the bracelet 16. The bracelet 16 further preferably includes one or more alert components for generating an alert on the bracelet 16 for the individual wearing the bracelet 16 when the bracelet is determined to be in proximity to the buoy 12. The alert components preferably include mechanisms for generating one or more of auditory and tactile feedback to the individual. In one embodiment, the alert components include a vibration motor 28 in electronic communication with the controller 24, the vibration motor 28 configured to cause the bracelet 16 to vibrate when an alert is generated. The bracelet 16 further preferably includes a speaker 30 in electronic communication with the controller 24 for emitting an audible alert to the individual wearing the bracelet 16 when an alert is generated. A battery 33 or other power source is also in communication with the controller 24 for powering components of the bracelet 16. Components of the bracelet 16 are preferably located within a housing 32 and the housing is preferably mounted on a band 34 such that the bracelet 16 may be worn on a wrist of the individual.

Figure 3:
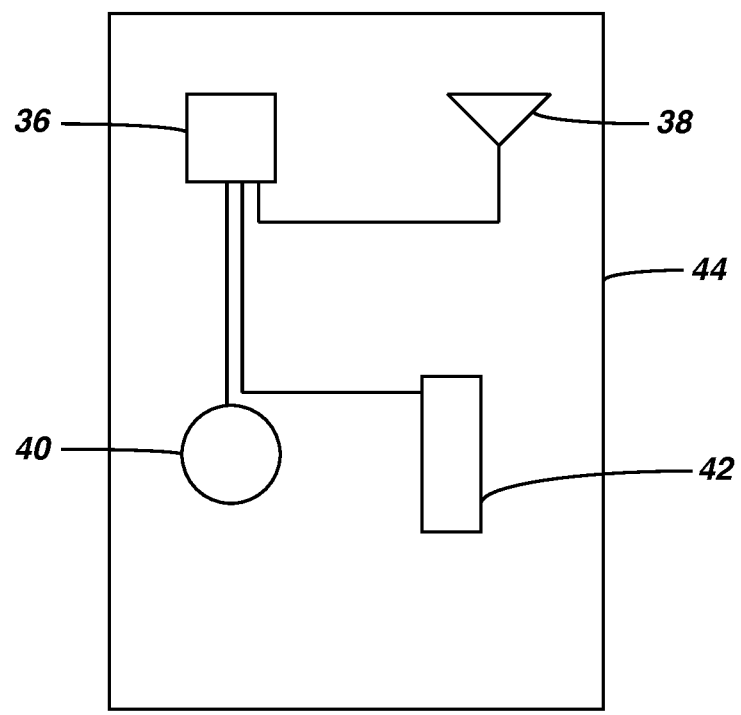
FIG. 3 show a diagram of a buoy of a behavior modification bracelet system according to one embodiment of the present disclosure.

Referring now to FIG. 3, the buoy 12 also includes a controller 36 that is in communication with components of the buoy 12. One or more antennas 38 are in communication with the controller 36 for communicating with the bracelet 16 and broadcasting a signal corresponding to the caution zone 18 defined around the buoy 12. The one or more antennas 38 may further enable the buoy 12 to communicate with the user device 20, such as via a Wi-Fi or cellular antenna. A speaker 40 is in communication with the controller 36 for emitting an audible alert from the buoy 12 when an incursion of the bracelet 16 into the caution zone 18 is detected. A power source 42 is in communication with the controller 36 for powering components of the buoy 12. Components of the buoy 12 are located within a buoy housing 44. The buoy housing 44 is preferably buoyant such that the buoy 12 may float within a body of water of interest.

Figure 4:
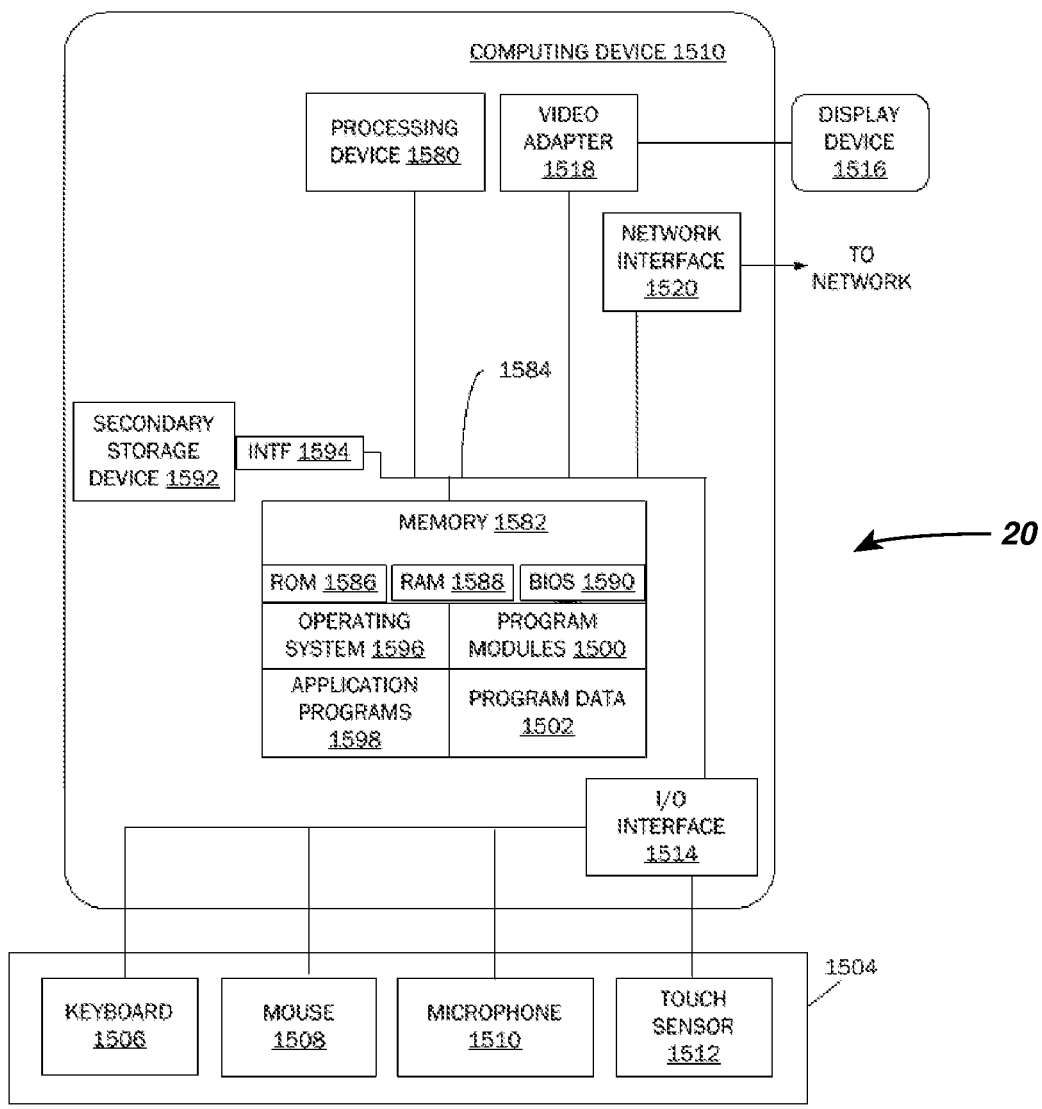
FIG. 4 shows a schematic diagram of a user device according to one embodiment of the present disclosure.

Referring to FIG. 4, examples of computing devices suitable for the user device 20 include a desktop computer, a laptop computer, a tablet computer, a mobile computing device (such as a smart phone, a tablet device, or other mobile devices), or other devices configured to process digital instructions.

The system memory 1582 includes read only memory 1586 and random-access memory 1588. A basic input/output system 1590 containing the basic routines that act to transfer information within computing device 1510, such as during start up, is typically stored in the read only memory 1586.

The computing device 1510 also includes a secondary storage device 1592 in some embodiments, such as a hard disk drive, for storing digital data. The secondary storage device 1592 is connected to the system bus 1584 by a secondary storage interface 1594. The secondary storage devices 1592 and their associated computer readable media provide nonvolatile storage of computer readable instructions (including application programs and program modules), data structures, and other data for the computing device 1510.

Although the exemplary environment described herein employs a hard disk drive as a secondary storage device, other types of computer readable storage media are used in other embodiments. Examples of these other types of computer readable storage media include magnetic cassettes, flash memory cards, digital video disks, Bernoulli cartridges, compact disc read only memories, digital versatile disk read only memories, random access memories, or read only memories. Some embodiments include non-transitory media. Additionally, such computer readable storage media can include local storage or cloud-based storage.

A number of program modules can be stored in secondary storage device 1592 or memory 1582, including an operating system 1596, one or more application programs 1598, other program modules 1500 (such as the software engines described herein), and program data 1502. The computing device 1510 can utilize any suitable operating system, such as Microsoft Windows™ Google Chrome™, Apple OS, Linux, Unix, and any other operating system suitable for a computing device. Other examples can include Microsoft, Google, or Apple operating systems, or any other suitable operating system used in computing devices.

In some embodiments, a user provides inputs to the computing device 1510 through one or more input devices 1504. Examples of input devices 1504 include a keyboard 1506, mouse 1508, microphone 1510, and touch sensor 1512 (such as a touchpad or touch sensitive display). Other embodiments include other input devices 1504. The input devices are often connected to the processing device 1580 through an input/output interface 1514 that is coupled to the system bus 1584. These input devices 1504 can be connected by any number of input/output interfaces, such as a parallel port, serial port, game port, or a universal serial bus. Wireless communication between input devices and the interface 1514 is possible as well, and includes infrared, BLUETOOTH® wireless technology, 802.11a/b/g/n, cellular, or other radio frequency communication systems in some possible embodiments.

In this example embodiment, a display device 1516, such as a monitor, liquid crystal display device, projector, or touch sensitive display device, is also connected to the system bus 1584 via an interface, such as a video adapter 1518. In addition to the display device 1516, the computing device 1510 can include various other peripheral devices (not shown), such as speakers or a printer.

When used in a local area networking environment or a wide area networking environment (such as the Internet), the computing device 1510 is typically connected to a network through a network interface 1520, such as an Ethernet interface. Other possible embodiments use other communication devices. For example, some embodiments of the computing device 1510 include a modem for communicating across the network.

The computing device 1510 typically includes at least some form of computer readable media. Computer readable media includes any available media that can be accessed by the computing device 1510. By way of example, computer readable media include computer readable storage media and computer readable communication media.

Computer readable storage media includes volatile and nonvolatile, removable and non-removable media implemented in any device configured to store information such as computer readable instructions, data structures, program modules or other data. Computer readable storage media includes, but is not limited to, random access memory, read only memory, electrically erasable programmable read only memory, flash memory or other memory technology, compact disc read only memory, digital versatile disks or other optical storage, magnetic cassettes, magnetic tape, magnetic disk storage or other magnetic storage devices, or any other medium that can be used to store the desired information and that can be accessed by the computing device 1510.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are also included within the scope of computer readable media.

The computing device illustrated in FIG. 4 is also an example of programmable electronics, which may include one or more such computing devices, and when multiple computing devices are included, such computing devices can be coupled together with a suitable data communication network so as to collectively perform the various functions, methods, or operations disclosed herein.

Figure 5:
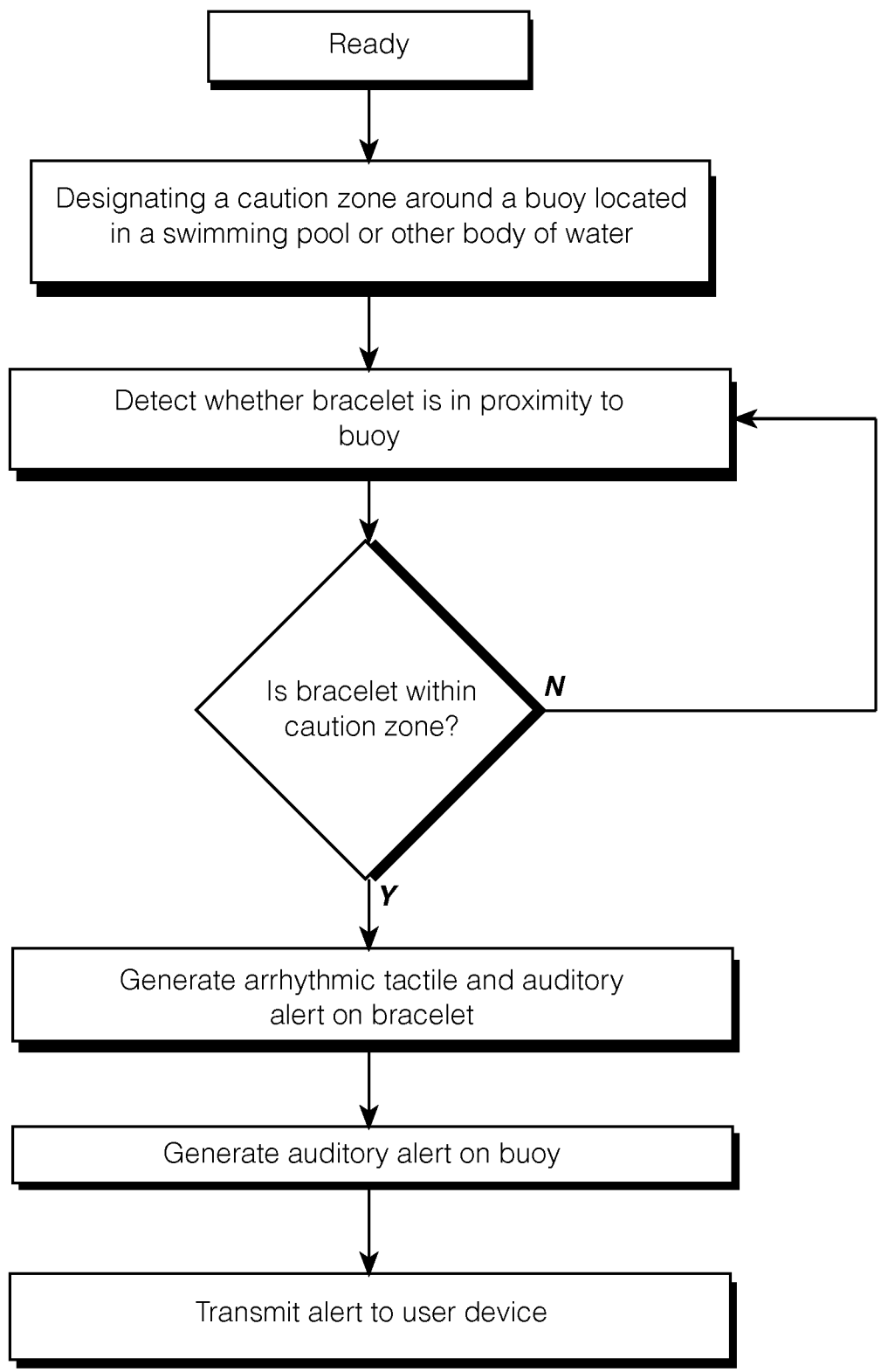
FIG. 5 is a flow chart showing methods of a behavior modification bracelet system according to one embodiment of the present disclosure.

In operation, the behavior modification bracelet system 10 detects whether the bracelet 16 has entered into an unsafe proximity to a body of water and generates alerts on the bracelet, buoy, and user device to warn of an unsafe proximity to the body of water. As shown in FIG. 5, a caution zone is designated around the buoy. The caution zone may correspond to a distance surrounding the buoy that is sufficiently sized to cover a perimeter of a swimming pool or other body of water. A presence of the bracelet is detected to determine whether the bracelet is in proximity to the caution zone. Using the user device, an operator may designate a safe distance around the caution zone before an alert is generated. If the bracelet is detected to be in an unsafe proximity to the buoy, one or more of a tactile and auditory alert is generated on the bracelet. The tactile alert is preferably arrhythmic such that the alert is particularly stimulating to an individual with ASD. An audible alert is further generated on the buoy, and an alert may be transmitted to and displayed on the user device.

Advantages of the behavior modification bracelet system include the specific ability to deter those with ASD from a body of water such as a swimming pool. While existing devices are available to alert of the incursion of a person into a caution zone near a body of water, those devices are not configured to specifically deter those with ASD from approaching the body of water without supervision. Further, an alert is generated not only on the bracelet to warn the wearer of the bracelet but also on the buoy within the body of water to warn any bystanders of an incursion into the caution zone. Existing products are designed to locate a child; however those products do not operate to discourage a child from entering a caution zone. Embodiments of the present disclosure deter a child from entering the caution zone through a learning process that occurs through behavioral science.

The foregoing description of preferred embodiments of the present disclosure has been presented for purposes of illustration and description. The described preferred embodiments are not intended to be exhaustive or to limit the scope of the disclosure to the precise form(s) disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the concepts revealed in the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

What is claimed is:

1. A behavior modification system for deterring an individual with autism spectrum disorder from entering an area of a caution zone, the behavior modification system comprising:
   a bracelet worn by the individual and including a bracelet controller, an antenna in communication with the bracelet controller, an alert component having a vibration motor in communication with the bracelet controller for providing an alert to the wearer of the bracelet, and a power supply in communication with the bracelet controller;
   at least one base unit including a controller, the at least one base unit in communication with the bracelet, the base unit associated with the area of the caution zone;
   wherein when the controller of the bracelet determines that the bracelet is located within the area of the caution zone associated with the at least one base unit, the alert component generates an alert sensed by the wearer of the bracelet, the alert including one or more of arrhythmic vibrations felt by the wearer of the bracelet generated by the vibration motor and audible sounds audible to the wearer of the bracelet that are unpleasant to the individual with autism spectrum disorder.

2. The behavior modification system of claim 1, wherein the alert component of the bracelet comprises a speaker in communication with the controller.

3. The behavior modification system of claim 1, wherein the alert component of the bracelet further comprises a power source in communication with the controller.

4. The behavior modification system of claim 1, the bracelet further comprising a GPS module in communication with the controller, wherein the bracelet transmits a geographic location of the bracelet via the GPS module.

5. The behavior modification system of claim 1, further comprising a user device comprising a display, one or more inputs, and a processor, the user device in communication with the bracelet and base unit via a network.

6. The behavior modification system of claim 5, wherein the alert is displayed on the user device when the bracelet is determined to be within the area of the caution zone.

7. The behavior modification system of claim 5, wherein the area of the caution zone may be designated based on input from the user device.

8. The behavior modification system of claim 1, wherein the bracelet and base unit communicate via Bluetooth.

9. The behavior modification system of claim 1, the base unit comprising a buoy configured to float within a body of water defined by the caution zone.

10. A method of deterring entry of an individual within a caution zone, the method comprising:
    providing a bracelet including an antenna, alert components including at least one vibration motor, speaker, power source and a controller in communication with the antenna and the alert components;
    providing at least one base unit in communication with the bracelet, the base unit associated with a predetermined caution zone;
    defining a caution zone associated with the at least one base unit, the caution zone corresponding to the predetermined caution zone;
    generating an arrhythmic alert on the alert component of the bracelet felt by a wearer of the bracelet when the bracelet is determined to be within the caution zone associated with the at least one base unit; and
    generating an audible alert audible to the wearer of the bracelet on the at least one base unit when the bracelet is determined to be in proximity to the caution zone around the at least one base unit.

11. The method of claim 10, wherein the alert generated on the bracelet is the arrhythmic alert generated by the vibration motor of the bracelet.

* * * * *